(12) United States Patent
Carr et al.

(10) Patent No.: US 6,423,868 B1
(45) Date of Patent: Jul. 23, 2002

(54) PROCESS FOR THE PRODUCTION OF AN AQUEOUS MONOESTER PEROXYCARBOXYLIC ACID SOLUTION, THE SOLUTION OBTAINABLE BY THIS PROCESS, AND ITS USE AS DISINFECTANT

(75) Inventors: Graham Carr; Alun P. James, both of Liverpool (GB)

(73) Assignee: Solvay (Societe Anonyme), Brussels (BE)

( * ) Notice: Subject to any disclaimer, the term of this patent is extended or adjusted under 35 U.S.C. 154(b) by 0 days.

(21) Appl. No.: 09/720,101
(22) PCT Filed: Jun. 1, 1999
(86) PCT No.: PCT/EP99/03837
§ 371 (c)(1),
(2), (4) Date: Feb. 26, 2001
(87) PCT Pub. No.: WO99/67213
PCT Pub. Date: Dec. 29, 1999

(30) Foreign Application Priority Data

Jun. 22, 1998 (EP) .............................................. 98304892

(51) Int. Cl.$^7$ ........................ C07C 69/34; C07C 409/24
(52) U.S. Cl. ...................... 560/198; 560/198; 560/204; 560/302; 560/190; 562/2; 562/6; 510/367; 510/375; 510/376
(58) Field of Search ................................. 510/367, 375, 510/376; 560/180, 204, 198, 190, 302; 562/2, 6

(56) References Cited

PUBLICATIONS

Sherlock Swann, Jr. et al, "Ethyl Hydrogen Sebacate", Organic Synthesis Coll. vol. 2, A.H. Blatt, Ed., John Wiley & Sons (1943), pp. 276–277.*

* cited by examiner

Primary Examiner—Paul J. Killos
Assistant Examiner—Farhad Forohar
(74) Attorney, Agent, or Firm—Larson & Taylor PLC

(57) ABSTRACT

Process for the production of an aqueous monoester peroxycarboxylic acid solution by reaction of a peroxygen compound with at least one dicarboxylic acid and with at least one alcohol optionally in the presence of an acid catalyst. Aqueous monoester peroxycarboxylic acid solution obtainable by this process. Use of the aqueous monoester peroxycarboxylic acid solution as disinfectant.

6 Claims, No Drawings

PROCESS FOR THE PRODUCTION OF AN AQUEOUS MONOESTER PEROXYCARBOXYLIC ACID SOLUTION, THE SOLUTION OBTAINABLE BY THIS PROCESS, AND ITS USE AS DISINFECTANT

The present invention is related to a process for the production of an aqueous monoester peroxycarboxylic acid solution. It also concerns the aqueous monoester peroxycarboxylic acid solution obtainable by this process and its use in disinfectant compositions.

Compositions containing monoester percarboxylic acids and their preparation by reaction between a monoester of an aliphatic dicarboxylic acid and hydrogen peroxide have been described in the international patent application WO 95/34537 to SOLVAY INTEROX LIMITED. Such compositions were shown to have no discernible odour and to be effective as microbicide. Although the compositions exhibited a level of available oxygen stability that would enable them to remain effective during several months storage, there is a continuing need to find new solutions of monoester percarboxylic acids.

It is an object of the invention to provide a new or alternative process for the production of monoester peroxycarboxylic acid solutions as well as to provide new monoester peroxycarboxylic acid solutions.

Consequently, the present invention concerns a process for the production of an aqueous monoester peroxycarboxylic acid solution by reaction of a peroxygen compound with at least one polycarboxylic acid and with at least one alcohol optionally in the presence of an acid catalyst. Preferably, the polycarboxylic acid is a dicarboxylic acid. While focused on this preferred embodiment, the present invention is however not limited thereto.

One of the essential characteristics of the process of the invention resides in the nature of the starting materials especially the dicarboxylic acid and the alcohol which render the process particularly performing. Indeed, by using these starting materials new solutions can be produced. It will be recognised that a complex mixture will be obtained using the process according to the invention containing the desired monoester peroxycarboxylic acid (called ester peracid hereafter), water, and may also contain residual amounts of non consumed dicarboxylic acid (called diacid hereafter), peroxygen compound, alcohol and optional acid catalyst, and in situ generated corresponding diester, monoester carboxylic acid, monocarboxylic peroxycarboxylic acid and diperoxycarboxylic acid. The advantage of the process of the invention resides in the possibility to control the relative amounts of the desired ester peracid to all the other products generated in situ. Indeed, by varying the amount of alcohol in the reaction mixture, more or less of the ester peracid will be produced relative to the amount of other products. So, a large variety of solutions can be obtained using a single process.

Another advantage resulting from the nature of the stating materials resides in the duration of the process. Indeed, the diacids used as starting material in the present invention have generally a higher solubility in the reaction mixture than have monoesters of dicarboxylic acids which are used in the known process described in the international patent application WO 95/34537. The higher solubility results in faster dissolution rates and thus shorter production times.

Yet another advantage of the process of the invention resides in the availability of the stating materials. Indeed, diacids and alcohols are more readily available than monoesters of a dicarboxylic acid.

Yet another advantage of the process of the present invention resides in the large choice of the organic radical of the ester group. Indeed, in the known process of the international patent application WO 95134537 the choice of the organic radical of the ester group is determined by the choice of the monoester of a dicarboxylic acid used as starting material whereas in the present invention the organic radical of the ester group originates from the alcohol It is clear that in the process of the invention alcohols can be used which are not available as monoesters.

The diacid used in the process of the invention can be chosen from any compound containing at least two carboxylic acid groups and which is capable of being transformed in an ester peracid in the process of the invention. The diacid can contain up to 20 carbon atoms, preferably up to 10 carbon atoms. The principal chain of the diacid which is substituted by the two carboxylic groups can be linear, branched, cyclic or aromatic, optionally unsaturated and or containing a heteroatom. Oxalic acid is convenient. Diacids with a linear principal chain generally corresponding to the formula COOH—R—COOH in which R is an alkylene group containing up to 6 carbon atoms can also be used. Suitable examples are adipic acid, glutaric acid and succinic acid. Examples of diacids with a branched principal chain are methyl succinic and ethyl malonic acids. Other examples are maleic, fumaric and maleic acids. The preferred diacids are adipic, glutaric and succinic acids. A mixture of two or more different diacids can be used in the process of the invention.

The diacid is generally used in an amount of at least 0,05% wt of the reaction mixture, preferably at least 5% wt The amount of diacid used is usually at most 65% wt in particular at most 25% wt. Quantities from 0,05 to 65% wt of diacid are convenient.

The peroxygen compound used in the process according to the invention can be chosen from hydrogen peroxide or any other peroxygen compound capable of releasing hydrogen peroxide in the reaction mixture of the process of the present invention. The expression "reaction mixture of the process of the invention" means a mixture containing water, the diacid, the alcohol, the peroxygen compound, optionally the acid catalyst, the ester peracid, the corresponding diester, monoester carboxylic acid, monocarboxylic peroxycarboxylic acid and diperoxycarboxylic acid. In particular, the peroxygen compound can be chosen from hydrogen peroxide, inorganic peracids, organic peracids and persalts. An example of inorganic peracid is Caro's acid. Organic acids containing up to 10 carbon atoms are convenient. An example of such an organic peracid is peracetic acid. Examples of persalts are sodium percarbonate and sodium perborate mono- or tetrahydrate. Hydrogen peroxide is preferred.

The peroxygen compound is generally used in an amount of at least 0,01% wt of the reaction mixture, in particular at least 5% wt. The amount of peroxygen compound used is usually at most 30% wt of the reaction mixture, preferably at most 25% wt. Quantities of peroxygen compound from 0,05 to 30% wt are convenient. When hydrogen peroxide is used, it can be added to the reaction mixture in the form of an aqueous solution containing from 1 to 85% wt of hydrogen peroxide. The molar ratio of the peroxygen compound to the diacid can be varied in a wide range. Generally this molar ratio is at least 0,1:1, preferably at least 1:1. The molar ratio is usually at most 35:1, in particular at most 7:1.

The alcohol used in the process of the invention can be chosen from any compound containing at least one hydroxyl group. Monoalcohols containing up to 20 carbon atoms are suitable, those containing up to 10 carbon atoms are preferred. Examples of suitable monoalcohols are methanol and ethanol. Diols containing up to 20 carbon atoms, preferably up to 10 carbon atoms can also be used. Examples of suitable diols are ethylene glycol and propylene glycoL. Polyols containing up to 20 carbon atoms can also be used. Examples of suitable polyols include sorbitol and mannitol. Alcohol ethoxylates could also be used. A mixture of two or more different alcohols can be used in the process of the invention.

The alcohol is generally used in an amount of at least 0,01% wt of the reaction mixture, in particular of at least 2% wt. The amount of alcohol used is usually at most 45% wt. more particularly at most 25% wt Quantities of alcohol from 0,05 to 45% wt are convenient. The molar ratio of the alcohol to the diacid can be varied within a wide range. Generally the ratio is at least 0,1:1, preferably at least 0,5:1. The molar ratio is usually at most 10:1, in particular at most 1:1.

The acid catalyst optionally used in the process of the invention can be an inorganic or organic acid having a pKa of about 3 or lower, and preferably having a pKa of below 1. It is particularly desirable to employ a non-halide mineral acid such as sulphuric or phosphoric or sulphamic acid or an organic sulphonic acid such as methyl or toluene sulphonic acid or a cation exchange resin doped with acid. Organic acids can also be used. Those containing up to 10 carbon atoms are convenient An example of organic acid is citric acid.

The catalyst is desirably used in a concentration of at least 0,05% wt in the reaction mixture, in particular at least 0,1% wt. The acid catalyst concentration is in many instances at most 10% wt especially at most 2,5% wt. Quantities of acid catalyst from 0,05 to 10% wt are convenient.

The invention process can be carried out at ambient temperature or at an elevated temperature. In practice the temperature can be at least 10° C., in particular at least 15° C. When it is desirable to achieve equilibration rapidly temperatures of at least 30° C. can be used. The temperature is commonly at most 60° C., especially at most 30° C.

The duration of the invention process can vary within a very wide range and depends on whether it is desired to obtain an equilibrium solution or a nonequilibrium solution. Equilibration can already be reached after a duration of at least 5 min. The duration is commonly at most 24 h.

The invention process can be carried out in any apparatus adequate for mixing the staring materials (diacid, peroxygen compound, alcohol, water and acid catalyst).

According to the process of the invention the starting materials (diacid, peroxygen compound, alcohol, water and acid catalyst) can be added in any order.

The reaction mixture can be stirred during the process of the invention.

The process of the invention is very useful for producing aqueous monoester peroxycarboxylic acid solutions containing the monoester peroxycarboxylic acid, water, residual amounts of non consumed peroxygen compound, dicarboxylic acid, alcohol and optional acid catalyst, and in situ generated corresponding diester, monoester carboxylic acid, monocarboxylic peroxycarboxylic acid and diperoxycarboxylic acid.

Consequently, the present invention also concerns aqueous monoester peroxycarboxylic acid solutions obtainable by the process described above containing the ester peracid, water, residual amounts of non consumed peroxygen compound, one or more diacids, one or more alcohols and optional acid catalyst, and in situ generated corresponding diester, monoester carboxylic acid, monocarboxylic peroxycarboxylic acid and diperoxycarboxylic acid. Particularly beneficial solutions are those obtainable by the process wherein the amounts of alcohol and diacid used are such that the molar ratio of hydroxy groups present in the alcohol to the carboxylic acid groups present in the diacid is different from 1.

The pH of the invention solutions can vary in a wide range. The pH is generally at least −2, most often at least 1. pH values of at most 8 are possible, values of at most 5 are preferred.

The concentration of ester peracid in the solution of the invention is generally at least 0,001% wt in particular at least 0,005% wt. The ester peracid concentration is usually at most 35% wt, especially at most 5% wt.

The amount of water present in the solution of the invention can vary within a very wide range since the solutions can be very dilute or very concentrated. The water content is commonly at least 10% wt. The amount of water is often at most 90% wt.

The solution of the invention contains in many cases residual amounts of non consumed peroxygen compound from 0,1 to 30% wt.

The diacid is usually present in the solution of the invention in a residual amount of at least 0,05% wt. The amount of diacid is commonly at most 10% wt The solution of the invention can contain a mixture of two or more different diacids.

If residual amounts of alcohol are found in the solution of the invention, these amounts are commonly at least 0,1% wt The amount of alcohol is often at most 10% wt. The solution of the invention can contain a mixture of two or more different alcohols.

The residual amount of optional acid catalyst that can be present in the solution of the invention is usually from 0 to 5% wt.

The solution of the invention can contain an amount of in situ generated diester from 0 to 5% wt.

The in situ generated monoester carboxylic acid can be present in the solution of the invention in an amount from 0 to 10% wt.

The concentration of in situ generated monocarboxylic peroxycarboxylic acid that can be found in the solution of the invention is often from 0 to 30% wt.

The amount of in situ generated diperoxycarboxylic acid that can be present in the solution of the invention is commonly from 0 to 10% wt.

Particularly beneficial solutions are those containing at least 0,01% wt of monoester peroxycarboxylic acid, at least 0,1% wt of peroxygen compound, at least 0,05% wt of dicarboxylic acid and at least 0,1% wt of alcohol The solution of the invention can contain other additives. These additives can be chosen from stabilisers, surfactants and thickeners. Such additives are often incorporated in an amount from 0,02 to 20%, and in many instances from 0,1 to 10% wt of the solution.

Suitable stabilisers include hydroxy substituted aromatic carboxylic acids and ester derivatives thereof particularly phenol carboxylic acids such as p-hydroxybenzoic acid and ester derivatives such as methyl or ethyl esters. They also include organic polyphosphonic acid sequestrants such as ethylidene diphosphonic acid, and aminopolymethylenephosphonic acids, pyridine carboxylic acids especially dipicolinic acid and mixtures thereof. In addition inorganic stabilisers may be used. An example of inorganic stabiliser is colloidal tin.

The surfactants can be nonionic, anionic or amphoteric. Surfctants can be soap or synthetic. Typical examples are described in chapter 2 of Synthetic Detergents by A. Davidson and B/M. Milwidsky, 6$^{th}$ Edition published in 1978 by George Godwin Limited. Cationic surfactants include quaternary ammonium salts, non-halide examples include sulphates, metosulphates, ethosulphates, hydroxides, acetates, saccharinates, phosphates and propionates.

Typical examples of suitable non-surfactant thickeners are cross linked polyacrylates, natural gums such as xanthan or rhamsan gum, cellulose derivatives such as carboxymethyl cellulose and silicates.

The solutions of the invention can also contain additional non-halide mineral acids. These acids can be selected from sulphuric, phosphoric or sulphamic acid or an organic sulphonic acid. The acid can be present at a concentration from 0,05 to 10% wt in the solution.

Particularly desirable solutions are those containing up to 20% wt of surfactant, from 0,025 to 5% wt of stabiliser and from 0,05 to 10% wt of a non-halide mineral acid.

The solution of the invention can be advantageously used as disinfectant. The present invention concerns therefore also the use of the above described solutions as disinfectants. The method for disinfection according to the present invention comprises contacting the substrate to be disinfected with the solution as a storage stable aqueous acidic solution of an ester peracid or prepared from one. The solution may be employed with or without dilution. When compositions are diluted, dilution is usually chosen to give an ester peracid concentration in solution of between about 1 part per million and 10000 parts per million, depending on the substrate. The disinfecting method can use a wide range of temperatures, typically from about 4° C. to the boiling point of the disinfectant. The solution of the invention can be used in a range of disinfection applications: e.g. disinfection of microorganism contaminated aqueous media e.g. process waters containing bacteria, algae, yeasts and viruses from industries such as paper and pulp, food processing e.g. sugar refining, brewing, wine making, discharges from sewage treatment works, meat processing factories, carcase rendering and livestock rearing. Other substrates include irrigation water in the horticultural industry, contaminated cooling waters, and contaminated surfaces in e.g. food processing, horticulture, catering, domestic or hospital environments. The invention compositions can be used to treat crops and harvested plants or plant products.

The solutions of the invention may be used for other purposes where peracids are used, including bleaching or as a bleach additive in washing processes.

Having described the invention in general terms, specific embodiments thereof are described in greater detail by way of example.

EXAMPLE 1

A solution containing 14,04 g glutaric acid, 9,79 g ethanol, 17,65 g concentrated hydrogen peroxide (85,5% wt), 1 g concentrated sulphuric acid, 57,52 g demineralised water, 0,1 g p-hydroxy benzoic acid, 0,17 g of 1-hydroxyethane-1, 1-diphosphonic acid (Briquest ADPA 60A) was prepared with stirring, and allowed to reach equilibrium The molar ratio of ester peracid to monocarboxylic peroxycarboxylic acid found in the system was 1:8, measured by HPLC.

EXAMPLE 2

A solution was prepared by mixing and stirring 16,5 g glutaric acid, 8 g methanol, 17,65 g concentrated hydrogen peroxide (85% wt), 0,1 g parahydroxy benzoic acid, 0,2 g Briquest ADPA 60A, 1 g concentrated sulphuric acid, 56,6 g water. The solution was allowed to reach equilibrium. The molar ratio of ester peracid to monocarboxylic peroxycarboxylic acid found in the system was 1:3.

EXAMPLE 3

A solution was prepared as described in example 2 with a lower level of methanol, 3 g methanol in stead of 8 g, a lower level of Briquest ADPA 60A, 0,17 g instead of 0,2 g, a higher level of water, 61,6 g in stead of 56,6 g. The molar ratio of ester peracid to monocarboxylic peroxycarboxylic acid found in the system was 1:11.

EXAMPLE 4

A solution was prepared by mixing and stirring 16,5 g of a mixture of adipic, glutaric and succinic acids, 8 g of methanol, 17,65 g concentrated hydrogen peroxide (85% wt), 1 g concentrated sulphuric acid, 56,6 g demineralised water, stabilised with 0,1 g para-hydroxybenzoic acid and 0,17 g Briquest ADPA 60A. The solution was allowed to reach equilibrium. The presence of esters peracids was detected by HPLC.

What is claimed is:

1. A process for the production of an aqueous monoester peroxycarboxylic acid solution by reaction of a peroxygen compound with at least one polycarboxylic acid and with at least one alcohol optionally in the presence of an acid catalyst.

2. The process according to claim 1, wherein the polycarboxylic acid is a dicarboxylic acid containing up to 20 carbon atoms, and wherein the dicarboxylic acid is used in an amount from 0,05 to 65% wt.

3. The process according to claim 1, wherein the peroxygen compound is chosen from hydrogen peroxide, inorganic peracids, organic peracids, organic peracids, persalts, and wherein the peroxygen compound is used in an amount of 0,05 to 30% wt of the reaction mixture.

4. The process according to claim 1, wherein the alcohol is chosen from monoalcohols and dialcohols containing up to 20 carbon atoms, wherein the alcohol is used in an amount from 0,05 to 45% wt of the reaction mixture and wherein the molar ratio of alcohol to dicarboxylic acids is from 0,1:1 to 10:1.

5. The process according to claim 1, wherein an acid catalyst is used chosen from inorganic or organic acids having Pka of 3 or lower, and wherein the acid catalyst is used in an amount from 0,05 to 10% wt of the reaction mixture.

6. The process according to claim 1, wherein the alcohol is a polyol containing up to 20 carbon atoms, wherein the alcohol is used in an amount from 0,05 to 45% wt of the reaction mixture and wherein the molar ratio of alcohol to dicarboxylic acids is from 0,1:1 to 10:1.

* * * * *